US009886677B1

(12) United States Patent
Marr et al.

(10) Patent No.: US 9,886,677 B1
(45) Date of Patent: Feb. 6, 2018

(54) DATA CENTER LIFE-CYCLE TRACKING AND INTEGRATION

(71) Applicant: Amazon Technologies, Inc., Reno, NV (US)

(72) Inventors: Michael David Marr, Monroe, WA (US); Matthew D. Klein, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 1115 days.

(21) Appl. No.: 13/683,106

(22) Filed: Nov. 21, 2012

(51) Int. Cl.
*G06Q 10/08* (2012.01)
*G06Q 50/22* (2012.01)
*G06F 19/00* (2011.01)
*G06K 7/10* (2006.01)

(52) U.S. Cl.
CPC ......... *G06Q 10/087* (2013.01); *G06F 19/327* (2013.01); *G06K 7/10366* (2013.01); *G06Q 10/08* (2013.01); *G06Q 50/22* (2013.01)

(58) Field of Classification Search
CPC ...... G06Q 10/087; G06Q 10/08; G06Q 50/22; G06K 7/10366; G06F 19/327
USPC .......................................................... 705/28
See application file for complete search history.

(56) References Cited

U.S. PATENT DOCUMENTS 8,745,188 B2 * 6/2014 Westerfeld .............. H04L 43/10
709/223
2005/0289039 A1 * 12/2005 Greak ................ G06Q 30/0609
705/37

OTHER PUBLICATIONS

Bonneau, Vincent. The new markets of the Internet. Digiworld Yearbook, 115-133. Montpellier: Institut de l'Audiovisuel et de Telecommunications en Europe (IDATE), 2011.*

* cited by examiner

*Primary Examiner* — Ryan Zeender
*Assistant Examiner* — Fawaad Haider
(74) *Attorney, Agent, or Firm* — Thomas | Horstemeyer, LLP

(57) ABSTRACT

Disclosed are various embodiments for monitoring, maintaining, tracking, and/or integrating inventory items in one or more systems. An inventory integration system may monitor the states, dependencies, and/or locations of inventory items across one or more data centers and/or similar structures. Issues detected may be escalated and remedial actions to the issues may be generated. The inventory integration system may communicate with various external resources in order to convey various information associated with the items of inventory and/or the data centers.

20 Claims, 10 Drawing Sheets

DATA CENTER LIFE-CYCLE TRACKING AND INTEGRATION

BACKGROUND

With the emergence of cloud computing, demand for data centers and data center inventory is continuously expanding. As data centers expand, data center equipment identification, availability, and integration have become challenging processes.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

The present disclosure relates to monitoring, maintaining, tracking, and/or integrating inventory items in one or more systems. When one or more items of inventory reside in a data center, various issues may arise associated with the performance of the data center. For example, inventory items may fail before or after an average life span, and new equipment must be located and/or ordered in order to replace the failing inventory items.

Various goals associated with one or more data centers may exist. For example, it may by desirable to increase the capacity and/or bandwidth of a data center. Additionally, various external resources may need to access the various information associated with items of inventory and/or data centers. In the following discussion, a general description of the system and its components is provided, followed by a discussion of the operation of the same.

Figure 1A:
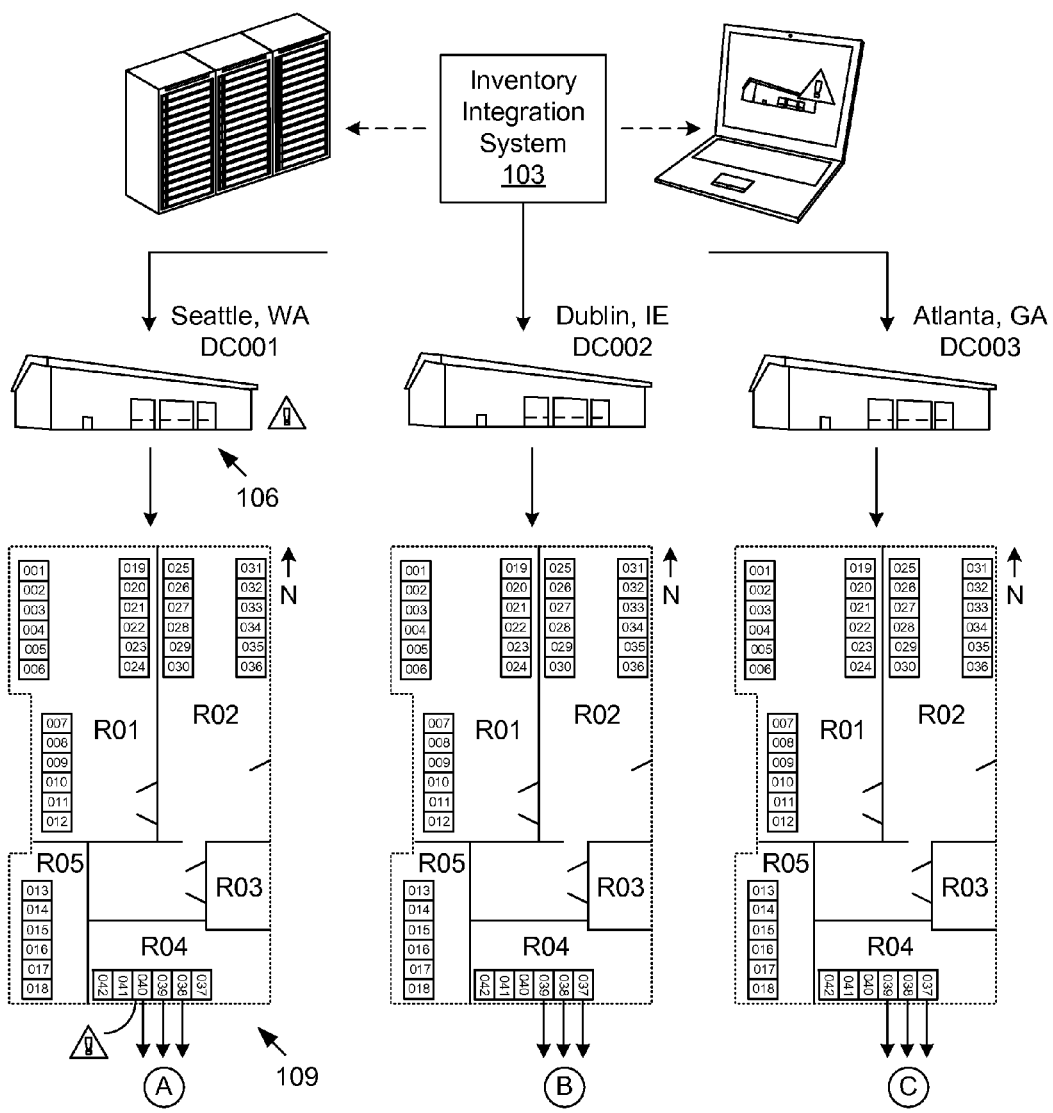
FIGS. 1A-B are drawings exemplifying a hierarchy of items of inventory according to where they may reside according to various embodiments of the present disclosure.
Figure 1B:
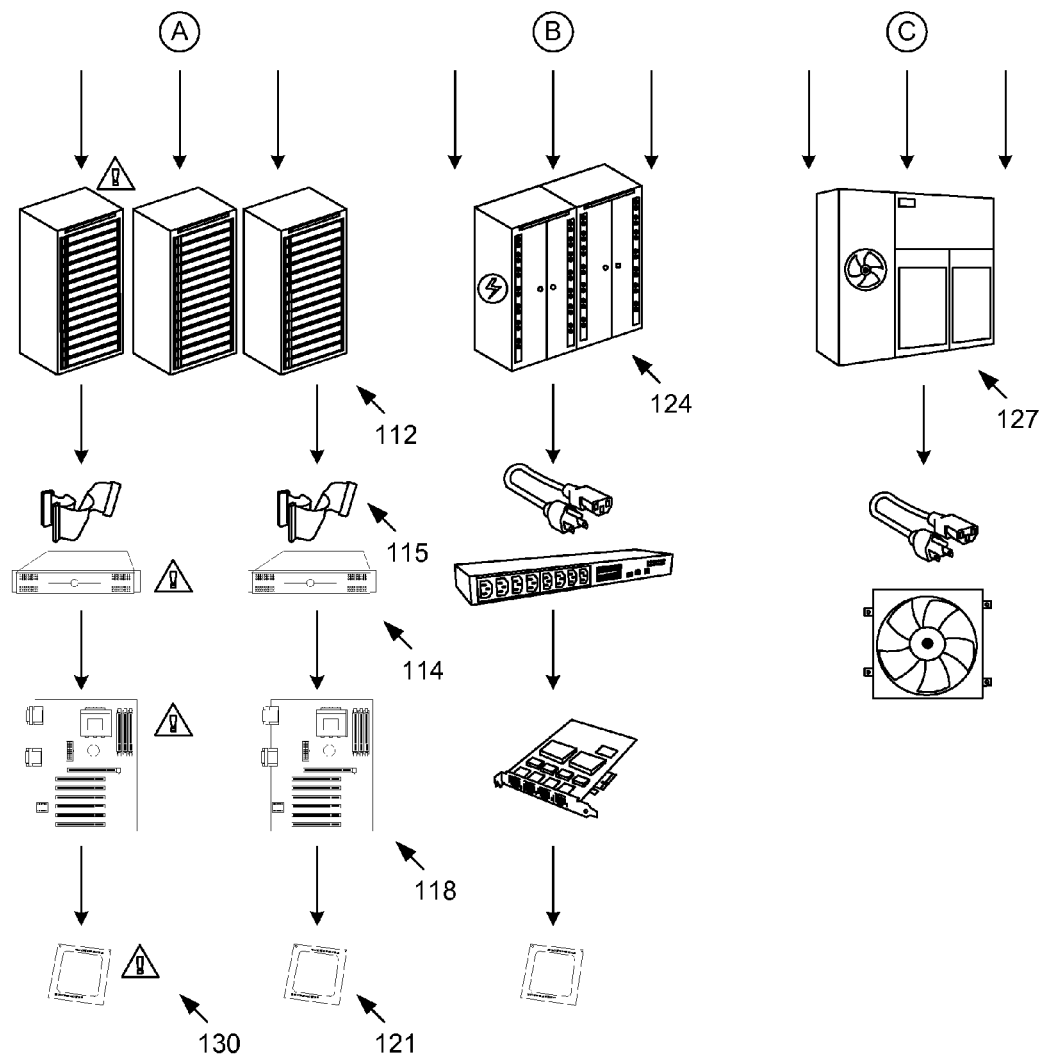

With reference to FIGS. 1A-B, shown is a pictorial representation of a hierarchy of items that may reside in a data center 106. At the highest level, the contents of the data center 106 may be monitored and integrated by an inventory integration system 103 in one or more client devices. The inventory integration system 103 may monitor one or more data centers 106 and/or the contents of the data centers 106. The floor plans 109 may be monitored by the inventory integration system 103 by determining which inventory items reside in particular locations in the floor plans 109. In FIG. 1B, a non-limiting example of the hierarchy of items that may reside in various location of a data center 106 is shown. For example, multiple server racks 112 may reside in one or more rooms in a data center 106. Inside the server racks 112, there may be various types of servers 114 and/or a variety of cables 115 used to connect the servers 114 to a network. Inside the servers 114, there may be one or more motherboards 118. On the motherboard 118, there may be one or more processors 121. Inventory items 230 may comprise other components, hard drives, solid state storage devices, network hardware, and/or any other inventory item.

Similarly, other items of inventory may reside in a data center 106. For example, a power distribution unit 124 and/or a computer room air conditioning unit 127, as well as its individual components shown below, may further reside in a data center 106. It is understood that the inventory integration system 103 may be able to detect issues associated with one or more items of inventory. For example, an icon 130 may indicate that an issue may exist with the example processor. The issue may be escalated by the inventory integration system 103 to any parent items that depend on the performance of the processor. As shown, the inventory integration system 103 may escalate the issue to the data center 106 level. The detected issues may be transmitted as a notification to one or more administrators. Additionally, the inventory integration system 103 may generate one or more user interfaces comprising information associated with the items of inventory, the data centers in which the items reside, metrics associated with the items of inventory, detected issues, and/or other information to be accessed by a client device. Responses to the one or more issues will be addressed in further detail below.

Figure 2:
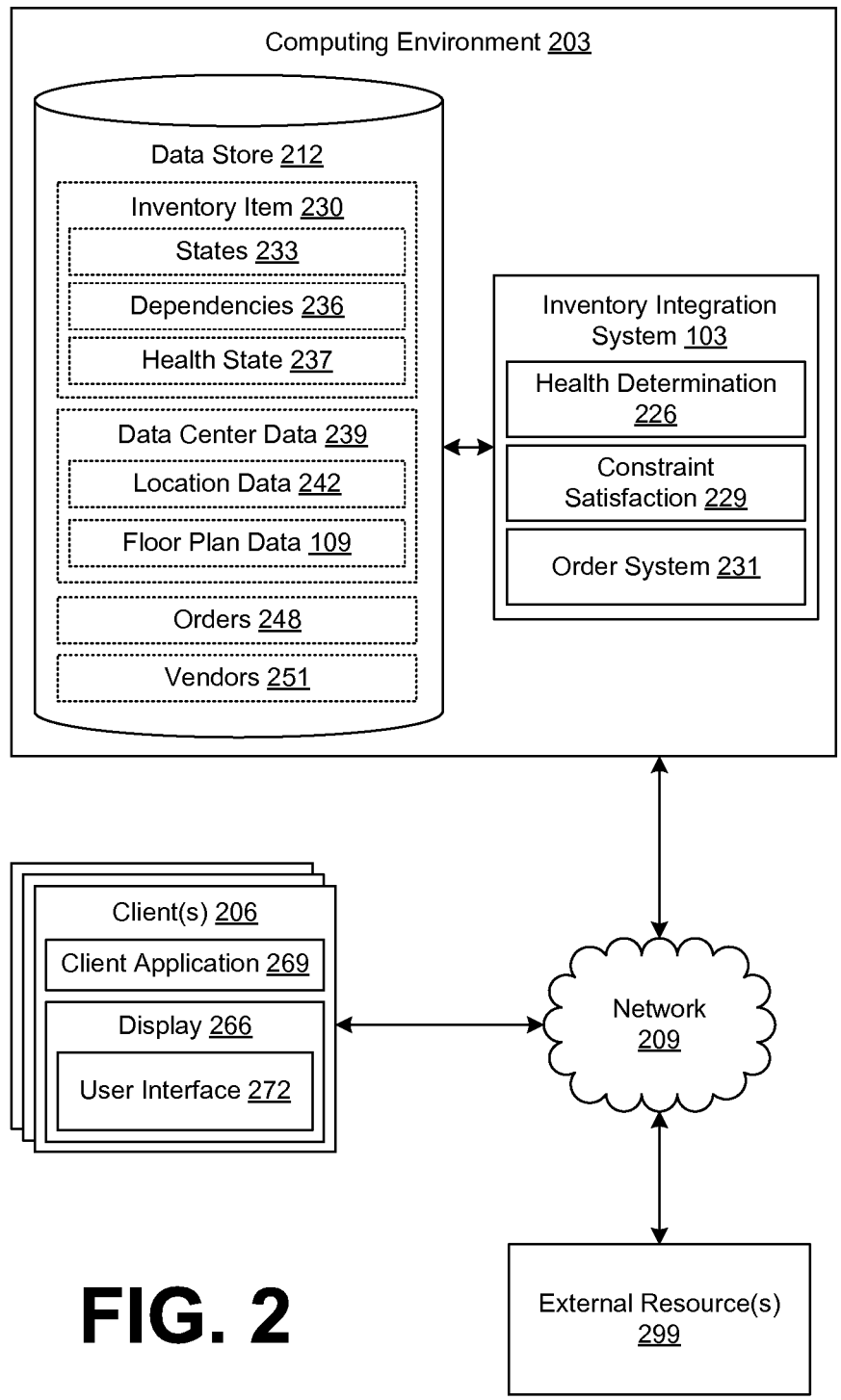
FIG. 2 is a drawing of an example networked environment according to various embodiments of the present disclosure.

With reference to FIG. 2, shown is a networked environment 200 according to various embodiments. The networked environment 200 includes a computing environment 203 in data communication with clients 206 and/or external resources 299 via a network 209. The network 209 includes, for example, the Internet, intranets, extranets, wide area networks (WANs), local area networks (LANs), wired networks, wireless networks, or other suitable networks, etc., or any combination of two or more such networks.

As illustrated by FIG. 2, in an embodiment the inventory integration system 103 can be executed in computing environment 203. The computing environment 203 may comprise, for example, a server computer or any other system providing computing capability. Alternatively, the computing environment 203 may employ a plurality of computing devices that may be employed that are arranged, for example, in one or more server banks or computer banks or other arrangements. Such computing devices may be located in a single installation or may be distributed among many different geographical locations. For example, the computing environment 203 may include a plurality of computing devices that together may comprise a cloud computing resource, a grid computing resource, and/or any other distributed computing arrangement. In some cases, the computing environment 203 may correspond to an elastic computing resource where the allotted capacity of processing, network, storage, or other computing-related resources may vary over time.

Various applications and/or other functionality may be executed in the computing environment 203 according to various embodiments. Also, various data is stored in a data store 212 that is accessible to the computing environment 203. The data store 212 may be representative of a plurality of data stores 212 as can be appreciated. The data stored in the data store 212, for example, is associated with the operation of the various applications and/or functional entities described below.

The components executed on the computing environment 203, for example, include an inventory integration system 103 and other applications, services, processes, systems, engines, or functionality not discussed in detail herein. The inventory integration system 103 is executed to monitor, maintain, track, and/or integrate inventory items 230 in one or more systems. For example, various items of inventory may reside in one or more data centers 106. Inventory items 230 may comprise both tangible and intangible items. For example, a server may be an inventory item 230 as well as a virtual server.

In order to determine whether an inventory item 230 and/or data center 106 has a probability of failing, a health state 237 may be generated by the inventory integration system 103. The generated health state 237 may be associated with an inventory item 230 and/or data center data 239. If the health state 237 meets one or more conditions, the inventory integration system 103 may generate a set of solutions and remedial actions to alleviate the risk to the data center 106 and/or may trigger various levels of alarms and/or may transmit various levels of notifications to administrators associated with the inventory item 230 and/or data center data 239 associated with the health state 237. Which level of alarm and/or notification transmitted may be based at least in part on an estimated urgency of the issue, the total number or monetary values of the inventory items 230 impacted, and/or the rate of change of the health state 237. For example, a natural disaster may disable power to a data center 106 and a backup generator residing the data center 106 may fail. It is understood that the health state 237 may lessen upon the occurrence of the power failure and the failure of the generator. Because the health state 237 may be low and the change occurred at a very fast rate, the system may issue a higher level of notification and/or alarm.

The inventory integration system 103 may generate one or more user interfaces 272 to facilitate the movement of inventory items 230 among the data centers 106, the purchase of new inventory items 230, the manual entry of health states 237, the availability and/or usage of physical locations in data centers 106, and/or various other functions.

The data stored in the data store 212 includes, for example, data associated with one or more inventory items 230, data centers 106, orders 248, vendors 251, and/or potentially other data. Data representing the inventory item 230 is any data associated with a tangible or intangible item of inventory and/or any relevant information associated with the inventory items 230. For example, inventory items 230 may include real estate, equipment, software, and/or any other items. Data relating to an inventory item 230 may further include states 233, dependencies 236, lifespans, health states 237, and/or other information associated with one or more inventory items 230. For example, a state 233 of an inventory item 230 may indicate that the inventory item 230 is idle, in use at a particular data center 106 and/or other business unit, and/or in the process of being ordered and/or delivered, or other states 233. The dependencies 236 may correspond to additional inventory items 230, engineering requirements, location requirements, and/or other constraints that may also be necessary in order for an inventory item 230 to function properly. For example, a server may require dependencies 236 such as a server rack, an assortment of cables, a power supply, and equipment with the necessary climate and/or power, etc. in order for the server to function properly. Additionally, non-physical items may be dependencies 236 such as an operating system, one or more virtual servers, software licenses, and/or any other intangible item that may also be necessary for an inventory item 230 to function properly.

A variety of data associated with data centers 106 may be stored in data store 212 as data center data 239 according to various embodiments. Such data may include the floor plans 109 and/or blueprints, climate capabilities, location 242, floor space usage and availability, and/or any other information associated with the data centers 106. Orders 248 stored in data store 212 may include data relating to orders placed by the inventory integration system 103 or by users through the inventory integration system 103. The data associated with orders 248 may include quantities of inventory items 230 ordered, destination data centers 106, destination addresses, requested shipping service level, shipping instructions, special handling instructions, packaging instructions and other options, payment instruments, status, contact information, and/or other data. Vendors 251 may include data relating to sellers of inventory items 230 such as, for example, vendor name, account information, payment instruments, billing addresses, destination addresses, contact information, inventory items 230 previously ordered and other order history data, vendor diversification requirements, and/or other data.

The client 206 is representative of a plurality of client devices that may be coupled to the network 209. The client 206 may comprise, for example, a processor-based system such as a computer system. Such a computer system may be embodied in the form of a desktop computer, a laptop computer, personal digital assistants, cellular telephones, smartphones, set-top boxes, music players, web pads, tablet computer systems, game consoles, electronic book readers, or other devices with like capability. The client 206 may include a display 266. The display 266 may comprise, for example, one or more devices such as liquid crystal display (LCD) displays, gas plasma-based flat panel displays, organic light emitting diode (OLED) displays, LCD projectors, or other types of display devices, etc.

The client 206 may be configured to execute various applications such as a client application 269 and/or other applications. The client application 269 may be executed in a client 206, for example, to access network content served by the computing environment 203 and/or other servers, thereby rendering a user interface 272 on the display 266. The client application may, for example, correspond to a browser, a mobile application, etc., and the user interface 272 may correspond to a network page, a mobile application screen, etc. The client 206 may be configured to execute applications beyond the client application 269 such as, for example, browsers, mobile applications, email applications, social networking applications, and/or other applications.

Next, a general description of the operation of the various components of the networked environment 200 is provided. To begin, it is understood that various items of inventory may exist in one or more data centers 106. The various items of inventory may include equipment residing in a data center 106, software running on the equipment, and/or other items in the data center 106. Inventory items 230 stored in data store 212 may correspond to these actual items of inventory.

As inventory items 230 fail, or are likely to fail, the inventory integration system 103 may generate one or more remedial actions and/or solutions to alleviate the risk. Such remedial actions may include repairing, reinstalling, adjusting an environmental condition, movement of the item from one location to another, purchasing or renewing a software license, and/or replacing an item. If replacement of an inventory item 230 is a solution, the inventory integration system 103 may recommend and/or initiate a transfer of similar inventory items 230 not in use. If the replacement of an inventory item 230 is not practical, the inventory integration system 103 may facilitate the order 248 of new inventory items 230 from one or more vendors 251, while maintaining a vendor diversification factor, via an order system 231. In order to quantify a degree of whether an inventory item 230 and/or data center 106 has a probability of failing, a health state 237 may be generated by the inventory integration system 103 through a health determination 226 component and associated with an inventory item 230 and/or a data center 106.

Additionally, various constraints may be determined and/or checked by a constraint satisfaction 229 component. For example, if a server has to be operated in a certain temperature range, the constraint satisfaction 229 component may determine whether a temperature where the serve resides (location 242) is in the certain temperature range or can be adjusted so that it falls within the range. If not, the health state 237 of the server and/or the data center 106 may be adjusted accordingly.

If the health state 237 indicates a problem, the inventory integration system 103 may trigger various levels of alarms and/or may transmit various levels of notifications to an administrator associated with the inventory item 230 and/or data center 106 associated with the health state 237. In another embodiment, the inventory integration system 103 may create tickets in a ticketing system to have an administrator resolve an issue.

Additionally, various goals may be set for one or more data centers 106 and/or for one or more inventory items 230. For example, it may be desired to increase the capacity and/or bandwidth of a data center 106. Accordingly, the capacity and/or bandwidth may be increased by adding one or more servers to the data center 106, upgrading or replacing archaic equipment, etc. A set of remedial actions may be generated by the inventory integration system 103 and may identify or flag one or more inventory items 230 based at least in part on the set of remedial actions. For example, one or more archaic servers in a data center 106 may be flagged to be replaced with a new model having more capacity. Upon replacement of the server with a new model, the flag may be removed.

It is understood that external resource(s) 299 may interact with the inventory integration system 103 by making requests for various information. The requests may pertain to information associated with data centers 106, inventory items 230, and/or other information. The inventory integration system 103 may authenticate and/or validate the request prior to fulfilling requests. Similarly, the inventory integration system 103 may make requests to external resources 299. For example, the inventory integration system 103 may make various requests and/or communicate with external resources 299 in order to update lists of vendors 251, vendor diversification requirements, and/or items offered for sale by vendors 251. The inventory integration system 103 may further encode and/or generate series of user interfaces 272, as discussed in greater detail below.

Next, a discussion of the computing environment 203 is provided in which the user interface 272 of FIG. 2 is generated followed by a discussion of the operation of the same.

Figure 3:
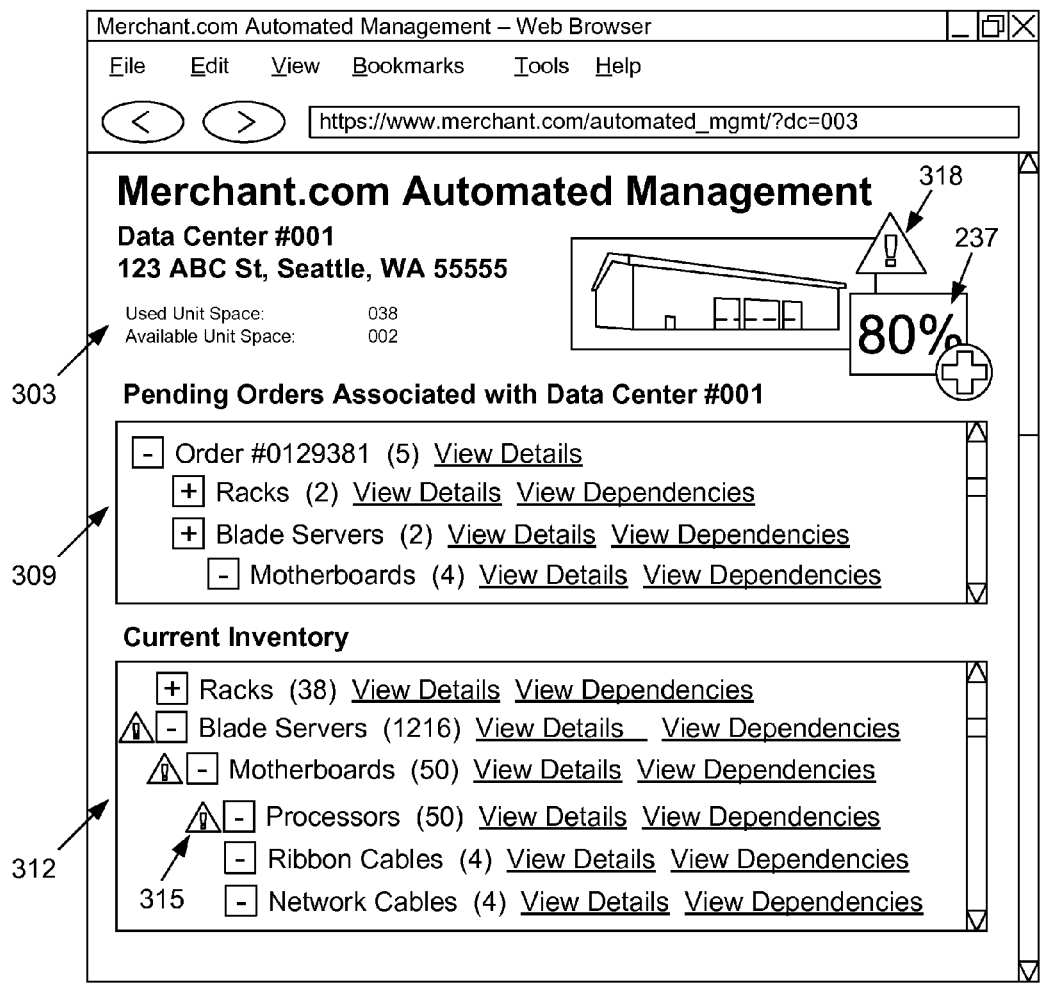
FIG. 3 is a drawing of an example user interface rendered by a client in the networked environment of FIG. 2 according to various embodiments of the present disclosure.

Referring next to FIG. 3, shown is an example of a user interface 272 rendered by the inventory integration system 103 in a client application 269 (FIG. 2) on a client 206 (FIG. 2) according to various embodiments. In this non-limiting example, the inventory integration system 103 permits a user to view information associated with the inventory items 230 (FIG. 2) represented as in a hierarchy. This example pertains to the items being used at a specific data center 106 (FIG. 1), for example, in Seattle. Various statistics associated with the data center 106 may be generated and/or shown. For example, statistics 303 identifies the number of unit spaces in use and/or available at the data center 106. Unit spaces may correspond to a physical location 242 (FIG. 2) in a data center 106, as may be appreciated. For example, a unit space may house one or more server racks, power distribution units, computer room air conditioning units, and/or other equipment. Various other statistics 303 may be determined and/or compiled, as may be appreciated.

An estimated health state 237 may be generated as a statistic of the data center 106. The estimated health state 237 may correspond to a vector, percentile, numeric value, pictorial representation, and/or any other means of showing an estimated health of a data center 106 and/or inventory item. In list 309, the pending orders associated with the data center may be shown. The inventory items 230 subject to an order may be rendered as a hierarchy, as may be appreciated. Similarly, in list 312, the inventory items currently residing in the data center 106 may be presented as a hierarchy. As shown, the lists may also show the low-level components of the data center 106, as may be appreciated. For example, a data center hierarchy may display all inventory items 230 in the data center 106 from server racks, to servers, to motherboards, to processors, to microchips on the processors, etc. By engaging "View Details," a series of pop-ups or additional user interfaces 272 may be rendered comprising details associated with the corresponding inventory item. For example, if a user engages "View Details" corresponding to the 50 processors in the data center 106, a listing of the processors and/or information associated with the processors may be shown.

An icon 315 associated with a level of urgency may be rendered where problems have been potentially identified and/or detected. In this non-limiting example, a potential issue associated with a processor in a motherboard has been detected. The parent inventory item, the motherboard, may be flagged as well. The flag may be escalated to grandparent, great-grandparent, etc. inventory items 230 up to the data center 106 as indicated by icon 318. By engaging "View Dependencies," inventory items 230 necessary for proper functionality of another item may be shown in pop-ups and/or as a progression of user interfaces 272, as may be appreciated. For example, in order for a motherboard to properly function, the motherboard may need properly connected processors, ribbon cables, and/or network cables.

Figure 4:
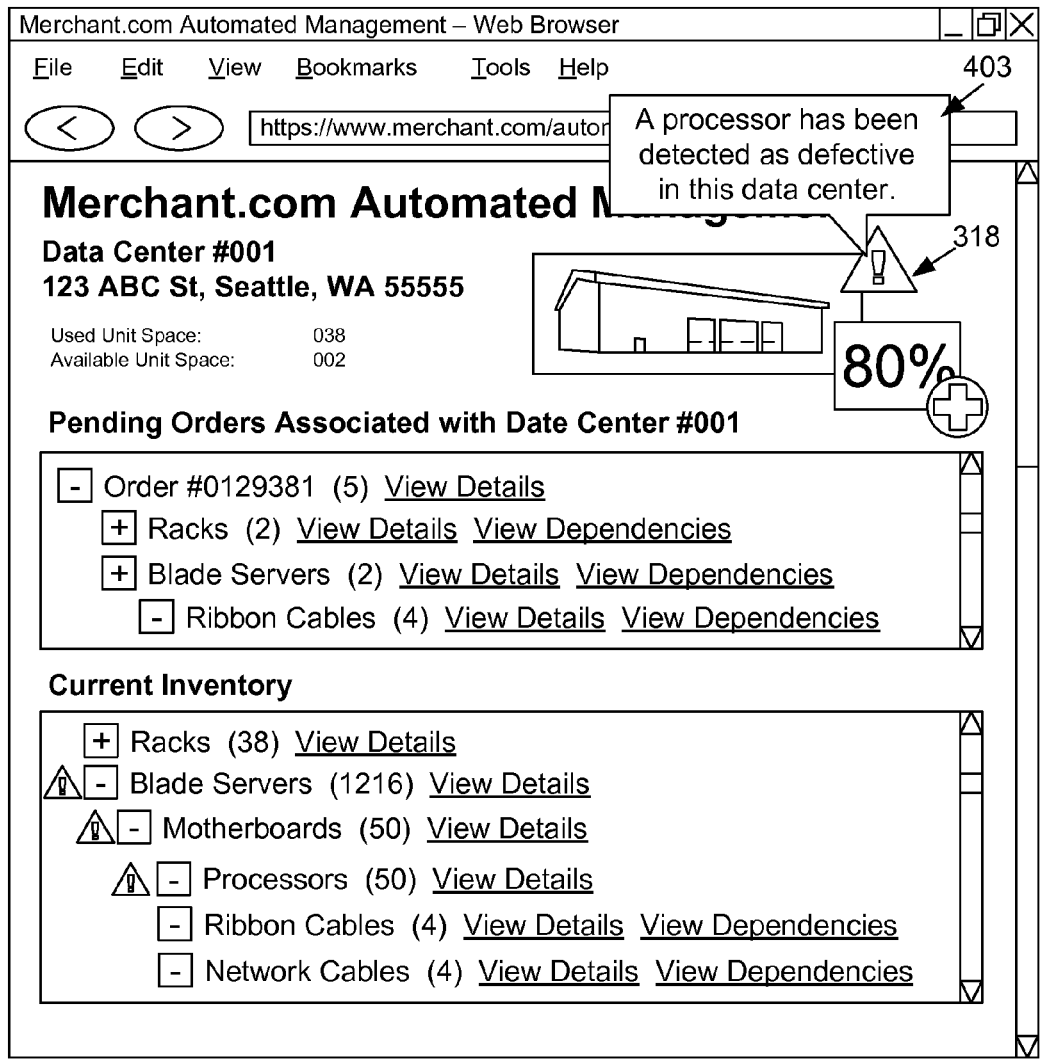
FIG. 4 is a drawing of an example user interface rendered by a client in the networked environment of FIG. 2 according to various embodiments of the present disclosure.

Turning now to FIG. 4, shown is an example of a user interface 272 rendered by the inventory integration system 103 in a client application 269 (FIG. 2) on a client 206 (FIG. 2) according to various embodiments. In this non-limiting example, a dialog box 403 may be generated when a user engages an icon 318 suggesting that something in the data center 106 has been flagged for review. In this non-limiting example, the dialog box 403 details that has "[a] processor has been marked as defective." It is understood that as a user engages similar icons, a dialog box or additional user interfaces 272 may be generated detailing the reason an inventory item and/or a data center 106 has been flagged. Additionally, remedial actions may be generated and/or provided that may be followed in order to alleviate an issue. Likewise, additional user interface elements may be generated to provide remedial action selections for administrators or other operators.

Figure 5:
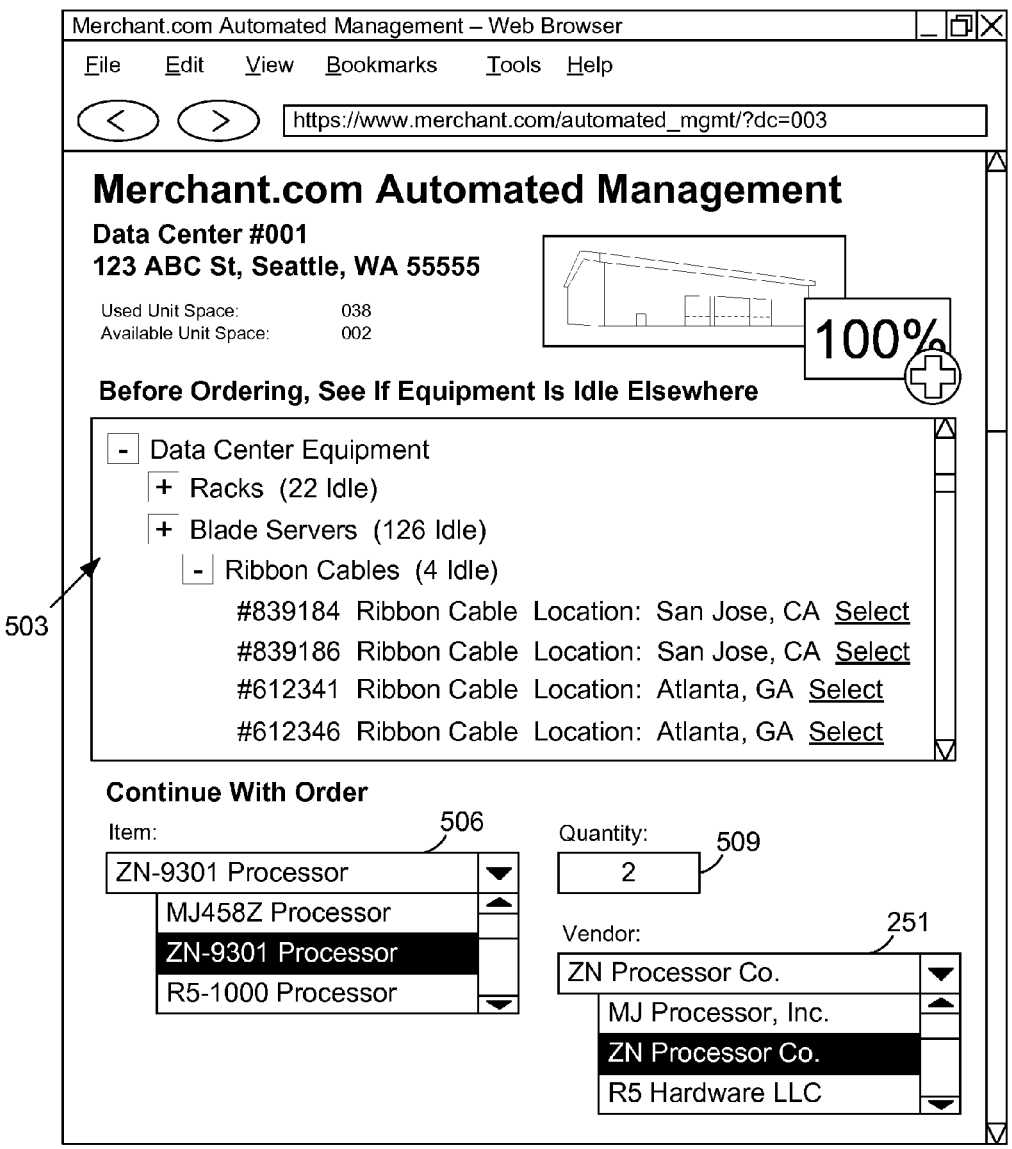
FIG. 5 is a drawing of an example user interface rendered by a client in the networked environment of FIG. 2 according to various embodiments of the present disclosure.

Moving on to FIG. 5, shown is an example of a user interface 272 rendered by the inventory integration system 103 in a client application 269 (FIG. 2) on a client 206 (FIG. 2) according to various embodiments. In this non-limiting example, the inventory integration system 103 may facilitate a manual ordering process by generating a user interface 272. A list 503 of available inventory items may be suggested to a user along with the locations of the inventory items while a user is conducting an order. It is understood that if a user were to select available inventory items, the inventory integration system 103 may generate a series of additional user interfaces 272 to initiate the process of shipping and/or reassigning one or more inventory items to a specified data center 106 (FIG. 1).

In order to reassign one or more inventory items 230 to a data center or other location, the inventory integration system 103 may reroute or rebalance the usage of existing inventory. For example, a bandwidth may be assigned and/or determined by the inventory integration system 103 and devoted to one set of systems (e.g., a cluster of servers). The bandwidth corresponding to one or more systems may be changed, for example, by modifying throttling configurations. The change in bandwidth of a system may be automatic. For example, if a set of switches corresponding to a system were to fail, the bandwidth of the system may be lowered by the inventory integration system 103 upon detection of the switches failing. To compensate for the drop in bandwidth of the first system, the bandwidth of one or more alternative systems may be increased. This may require rerouting or rebalancing existing inventory items 230 from one system to another. For example, one or more inventory items 230 may be reassigned to a new data center and, if applicable, the inventory integration system 103 may initiate the shipment or transfer of the one or more inventory items 230 to the new data center.

If no available inventory exists or reassigning existing inventory items is not feasible, the user may generate an order by selecting an item 506, a quantity 509, and/or a vendor 251. The inventory integration system 103 may suggest and/or require a user to specify a particular vendor 251 in order to meet vendor diversification requirements. Additionally, an order 248 (FIG. 2) may be limited by further constraints such as a budget, etc.

Figure 6:
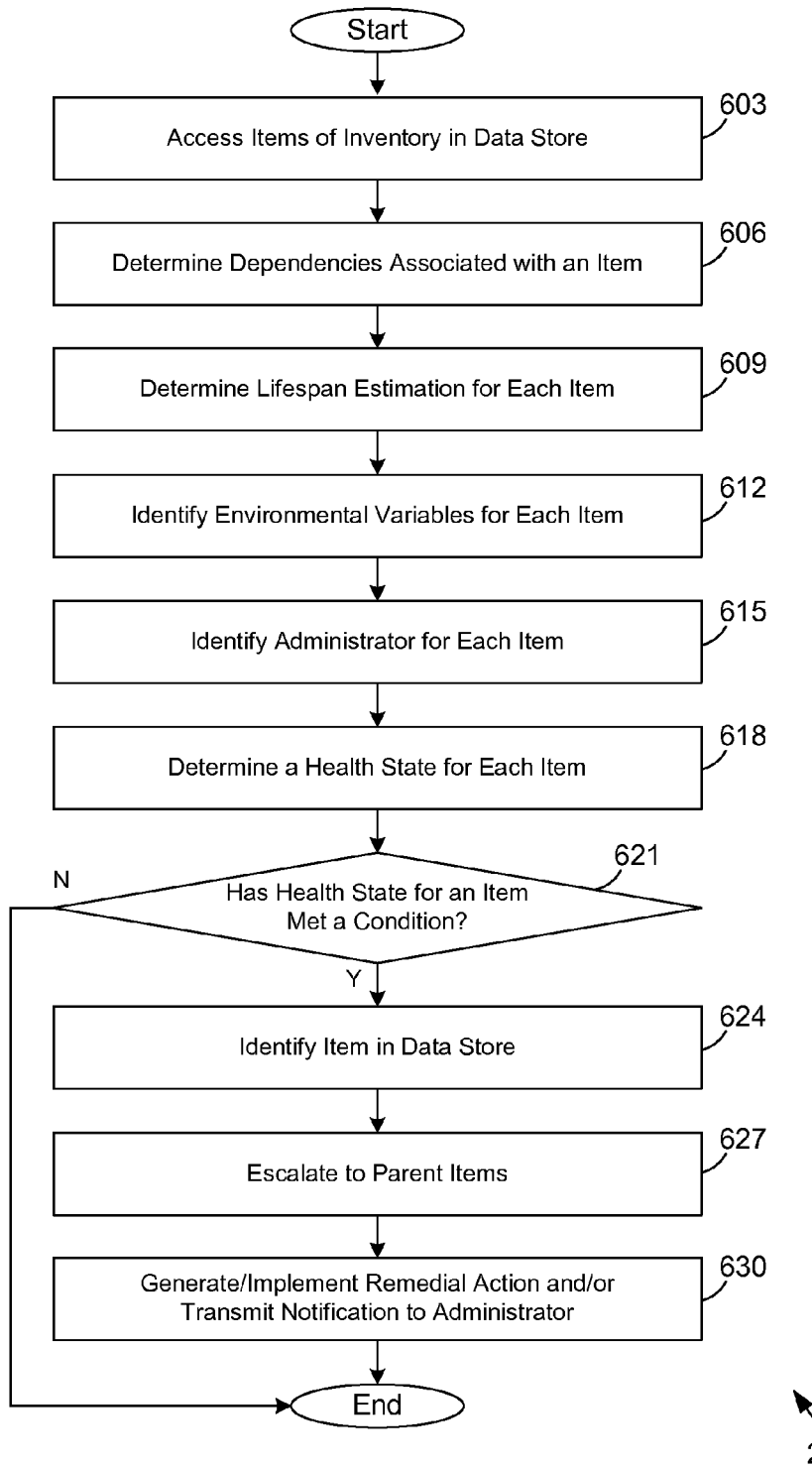
FIG. 6 is a flowchart illustrating one example of functionality implemented as portions of an inventory integration system, wherein the inventory integration system is executed in a computing environment in the networked environment of FIG. 2 according to various embodiments of the present disclosure.

Referring next to FIG. 6, shown is a flowchart that provides one example of the operation of a portion of the inventory integration system 103 (FIG. 2) according to various embodiments. It is understood that the flowchart of FIG. 6 provides merely an example of the many different types of functional arrangements that may be employed to implement the operation of the portion of the inventory integration system 103 as described herein. As an alternative, the flowchart of FIG. 6 may be viewed as depicting an example of steps of a method implemented in the computing environment 203 (FIG. 2) according to one or more embodiments.

Beginning with box 603, inventory items 230 (FIG. 2) in a data store 212 (FIG. 2) or in memory may be accessed and/or received by the inventory integration system 103. In box 606, the dependencies 236 (FIG. 2) associated with each inventory item 230 may be determined. For example, dependencies 236 correspond to additional inventory items 230, engineering requirements, location requirements, and/or other constraints that may also be necessary in order for an inventory item 230 to function properly. In box 609, a lifespan may be determined for each inventory item 230 based at least in part on an estimated lifespan of the item. For example, a server may have an estimated life expectancy of 10 years. In box 612, environmental variables for each item may be identified. For example, one or more particular servers may require the servers to be kept in a room with a certain temperature range.

In box 615, an administrator for each inventory item 230 may be determined. For example, a particular administrator may be associated with one or more particular inventory items 230. In box 618, a health state for each inventory item 230 may be determined. The health state may reflect the ability of an inventory item 230 to function properly for an estimated length of time. A health state may be represented as, for example, a health score. As a non-limiting example, if a server is older than the server's estimated lifespan, the server may be associated with a low health state 237 in anticipation that the server may fail. Alternatively, a relatively new server may be associated with a high health state 237. The health state 237 may further be determined by the dependencies 236 of the inventory item 230. For example, if an Ethernet card in a server has failed, the server in which the Ethernet card resides may be associated with a low health state 237 as well as the Ethernet card itself. A health state may depreciate based on the performance of the inventory item 230, the age of the inventory item 230, and/or any other information.

In box 621, it may be determined whether the health state for an inventory item 230 has met a condition. The condition may be predetermined and/or defined by a user or administrator. The condition may indicate, for example, whether a health state associated with an inventory item 230 has fallen to a point that the inventory item 230 has a relatively high probability of not remaining functional. For example, if a health state is represented as a health score, it may be determined whether the health score has met a condition or a threshold. Additionally, a condition may be set according to automatically determine whether an item 230 has reached a certain a certain state. For example, a state may be an age, temperature, version, and/or any other state of the item 230. In box 624, if the health state has met the condition, the inventory item 230 may be identified and/or flagged, for example, in the data store 212. In addition, parent items associated with the inventory item 230 may be identified and/or flagged, in box 627. For example, if a health state 237 of an inventory item 230 corresponding to an microprocessor meets a particular condition and/or threshold, the inventory item 230 may be identified and/or flagged as well as the motherboard in which the microprocessor resides.

A health state of an item 230 may be used in the determination of health states for other items 230. For example, if a plurality of the same model of servers fail at a certain environmental condition (e.g., the temperature or humidity of a room or rack in which the server resides), health states associated with servers with common components as the failing servers may be adjusted to reflect a likelihood that the operating servers may fail at their respective state. Accordingly, identification of conditions based on the health state of the items 230 may be used in correlating one condition to another condition based on a common component analysis.

Additionally, grandparent items may be identified and/or flagged. For example, the server in which the motherboard resides may be identified and/or flagged, the server rack in which the server resides may be identified and/or flagged, and so forth until the data center itself is identified and/or flagged. Finally, in box 630, a remedial action may be generated, identified, and/or suggested, and/or implemented. The remedial action may, for example, be a solution, when implemented, that would improve the health state of the item 230. A remedial action may further include transmitting a notification to the administrator identified in box 615. The notification may comprise, for example, the health state 237 and/or various information associated with the inventory item 230 with a health state 237 meeting the condition and/or threshold.

Figure 7:
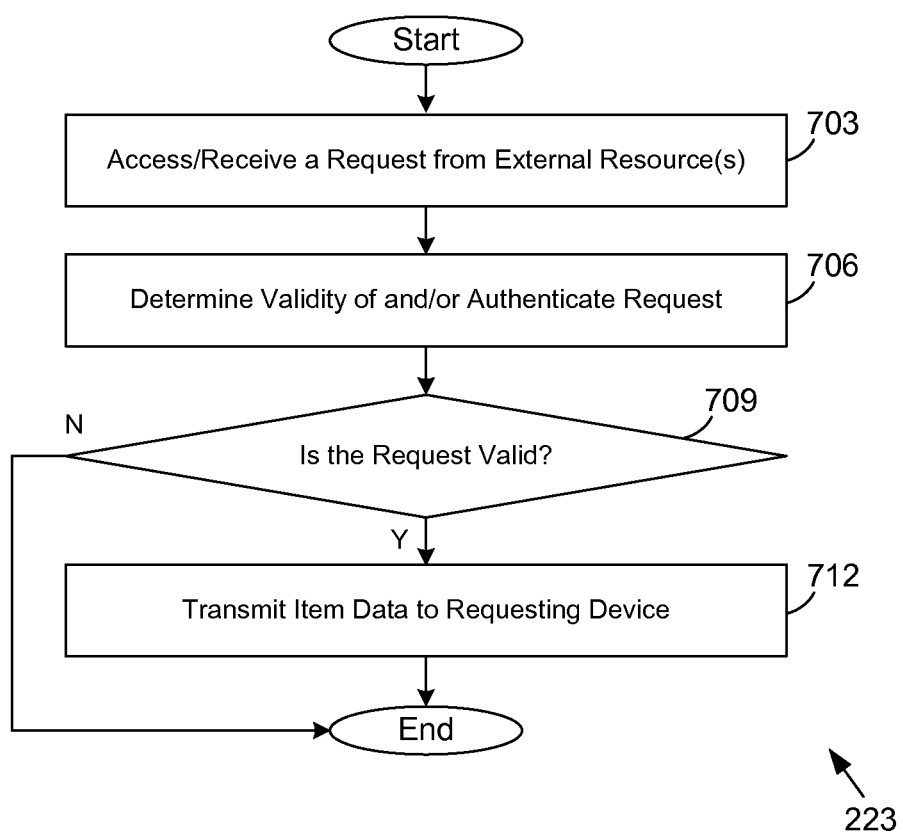
FIG. 7 is a flowchart illustrating one example of functionality implemented as portions of the inventory integration system executed in a computing environment in the networked environment of FIG. 2 according to various embodiments of the present disclosure.

Referring next to FIG. 7, shown is a flowchart that provides one example of the operation of a portion of the inventory integration system 103 interacting with external resources 299 (FIG. 2) according to various embodiments. It is understood that the flowchart of FIG. 7 provides merely an example of the many different types of functional arrangements that may be employed to implement the operation of the portion of the inventory integration system 103 as described herein. As an alternative, the flowchart of FIG. 7 may be viewed as depicting an example of steps of a method implemented in the computing environment 203 (FIG. 2) according to one or more embodiments.

Beginning with box 703, the inventory integration system 103 may receive and/or access a request from an external resource 299. For example, various systems may transmit requests in order to determine availability of inventory items 230 (FIG. 2), budget constraints, engineering constraints, and/or any other information. Next, in box 706, the request may be authenticated and/or a validity of the address may be determined. In box 709, if the request is determined to not be valid, the request may not be fulfilled. Alternatively, if the request is valid, in box 712, various data associated with the inventory items 230 may be transmitted to the requesting system and/or requesting computing device.

Figure 8:
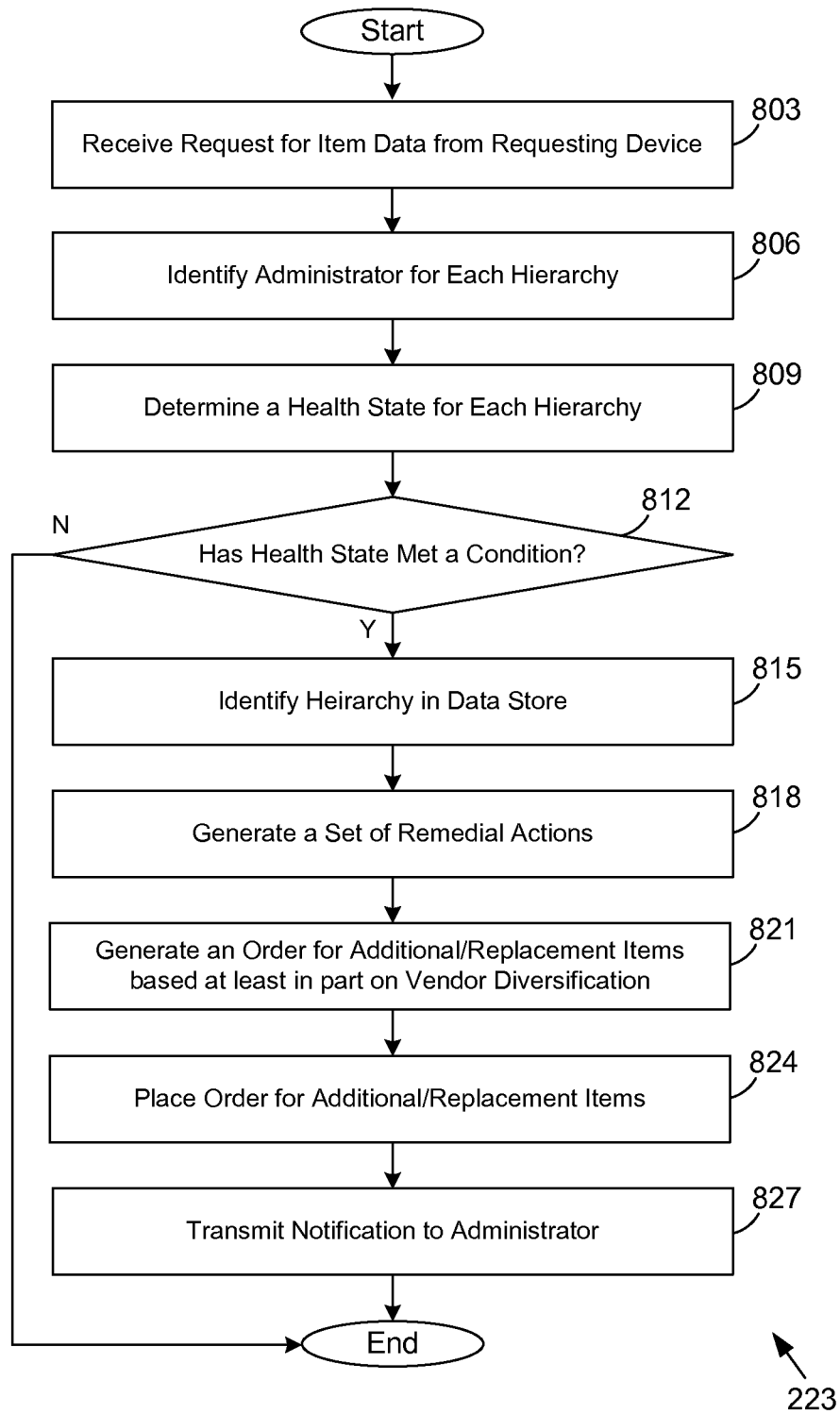
FIG. 8 is a flowchart illustrating one example of functionality implemented as portions of the inventory integration system executed in a computing environment in the networked environment of FIG. 2 according to various embodiments of the present disclosure.

Referring next to FIG. 8, shown is a flowchart that provides one example of the operation of a portion of the inventory integration system 103 according to various embodiments. It is understood that the flowchart of FIG. 8 provides merely an example of the many different types of functional arrangements that may be employed to implement the operation of the portion of the inventory integration system 103 as described herein. As an alternative, the flowchart of FIG. 8 may be viewed as depicting an example of steps of a method implemented in the computing environment 203 (FIG. 2) according to one or more embodiments.

As depicted in FIGS. 3-5, the inventory integration system 103 may generate a hierarchy of inventory items 230 (FIG. 2) that pictorially represents the inventory item 230 (FIG. 2) in association with other inventory items 230 from which an item may depend. In one embodiment, the pictorial representation of a hierarchy may resemble list 312 (FIG. 3). The hierarchy may comprise information associated with the inventory items 230 including, but not limited to, states 233 (FIG. 2), dependencies 236 (FIG. 2), and/or any other information associated with an inventory item 230.

Beginning with box 803, a request for data associated with one or more inventory items 230 may be received and/or accessed. Next, in box 806, an administrator associated with each hierarchy may be identified. For example, a particular administrator may be associated with one or more particular inventory items 230. In box 809, a health state may be determined for each of the hierarchies. In one embodiment, the health state may be represented as a health state 237 (FIG. 2). It is understood the health state may reflect the ability of the hierarchy, as a collective group of inventory items 230, to function properly for an estimated length of time. The health state associated with the hierarchy may deteriorate based on an analysis of the health state of respective inventory items 230 associated with the hierarchy. In box 812, it may be determined whether the health state for a hierarchy has met a condition. For example, if a health state is represented as a health state 237, it may be determined whether the health state 237 has met a condition and/or threshold. The condition may be predetermined and/or defined by a user or administrator. The condition may indicate, for example, whether a health state associated with a hierarchy has deteriorated to a point that the group of inventory items 230 has a relatively high probability of not remaining functional. For example, if a lone microprocessor fails in a lone motherboard residing in a server, the server has a high probability of failing. If a majority of the servers in a data center 106 are associated with low health states, a data center in which the servers reside may be associated with a health state reflecting the health state of the inventory items 230 residing in the data center 106.

In box 815, if the health state of a hierarchy has met the condition, the hierarchy itself or one or more of the inventory items 230 in the hierarchy may be identified and/or flagged, for example, in the data store 212 (FIG. 2). In box 818, a set of remedial actions and/or solutions may be generated based at least in part on the hierarchies and/or inventory items 230. For example, if a data center 106 is associated with a low health state, a set of solutions and remedial actions may be generated that, if followed, may improve the health state of the data center. As a non-limiting example, if a microprocessor in a server fails, the inventory integration system 103 may suggest that the microprocessor be replaced. In box 821, an order for additional and/or replacement inventory items 230 may be initiated and/or generated based at least in part on the set of remedial actions generated in box 818. For example, if one or more remedial actions suggests a replacement of a microprocessor, various microprocessors associated with an idle state 233 (FIG. 2) may be suggested to the user and/or a new of order of microprocessors may be facilitated. In box 824, the order may be placed automatically by the inventory integration system 103, based at least in part on the generated set of remedial actions, or the order may be initiated by a user or administrator.

It is understood that upon delivery and/or completion of an order, the new inventory items 230 may be added to the inventory. For example, an item may be inventory item 230 may be input by a scanning of a barcode and/or verification of receipt via a tracking number. Finally, in box 827, a notification may be sent to the administrator identified in box 806. The notification may comprise, for example, the health state 237 and/or various information associated with hierarchies and/or inventory items 230 with a health state 237 meeting the condition and/or threshold. If an order was placed, information associated with the order may be transmitted to the administrator.

Figure 9:
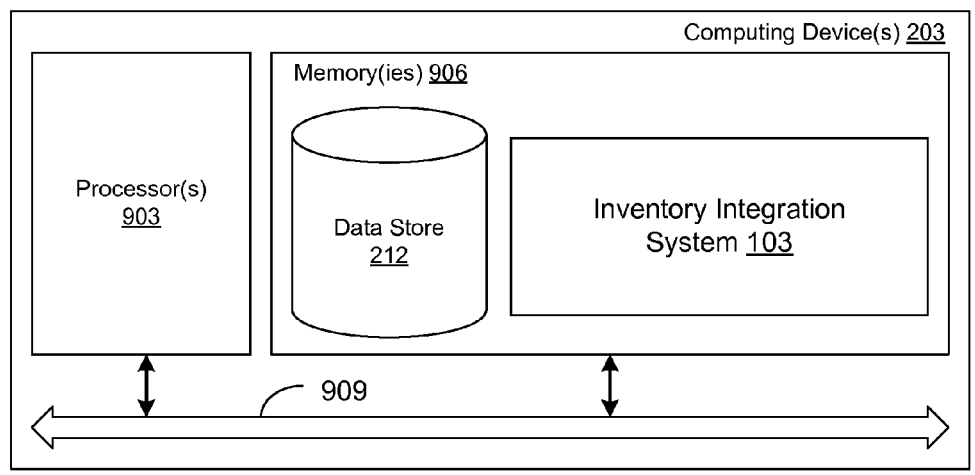
FIG. 9 is a schematic block diagram that provides one example illustration of a computing environment employed in the networked environment of FIG. 1 according to various embodiments of the present disclosure.

With reference to FIG. 9, shown is a schematic block diagram of the computing environment 203 according to an embodiment of the present disclosure. The computing environment 203 includes one or more computing devices 203. Each computing environment 203 includes at least one processor circuit, for example, having a processor 903 and a memory 906, both of which are coupled to a local interface 909. To this end, each computing environment 203 may comprise, for example, at least one server computer or like device. The local interface 909 may comprise, for example, a data bus with an accompanying address/control bus or other bus structure as can be appreciated.

Stored in the memory 906 are both data and several components that are executable by the processor 903. In particular, stored in the memory 906 and executable by the processor 903 are the inventory integration system 103 and potentially other applications. Also stored in the memory 906 may be a data store 212 and other data. In addition, an operating system may be stored in the memory 906 and executable by the processor 903.

It is understood that there may be other applications that are stored in the memory 906 and are executable by the processor 903 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory 906 and are executable by the processor 903. In this respect, the term "executable" means a program file that is in a form that can ultimately be run by the processor 903. Examples of executable programs may be, for example, a compiled program that can be translated into machine code in a format that can be loaded into a random access portion of the memory 906 and run by the processor 903, source code that may be expressed in proper format such as object code that is capable of being loaded into a random access portion of the memory 906 and executed by the processor 903, or source code that may be interpreted by another executable program to generate instructions in a random access portion of the memory 906 to be executed by the processor 903, etc. An executable program may be stored in any portion or component of the memory 906 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 906 is defined herein as including both volatile and nonvolatile memory and data storage components. Volatile components are those that do not retain data values upon loss of power. Nonvolatile components are those that retain data upon a loss of power. Thus, the memory 906 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 903 may represent multiple processors 903 and/or multiple processor cores and the memory 906 may represent multiple memories 906 that operate in parallel processing circuits, respectively. In such a case, the local interface 909 may be an appropriate network that facilitates communication between any two of the multiple processors 903, between any processor 903 and any of the memories 906, or between any two of the memories 906, etc. The local interface 909 may comprise additional systems designed to coordinate this communication, including, for example, performing load balancing. The processor 903 may be of electrical or of some other available construction.

Although an inventory integration system 103, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

The flowcharts of FIGS. 6, 7, and 8 show the functionality and operation of an implementation of portions of the inventory integration system 103. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 903 in a computer system or other system. The machine code may be converted from the source code, etc. If embodied in hardware, each block may represent a circuit or a number of interconnected circuits to implement the specified logical function(s).

Although the flowcharts of FIGS. 6, 7, and 8 show a specific order of execution, it is understood that the order of execution may differ from that which is depicted. For example, the order of execution of two or more blocks may be scrambled relative to the order shown. Also, two or more blocks shown in succession in FIGS. 6, 7, and 8 may be executed concurrently or with partial concurrence. Further, in some embodiments, one or more of the blocks shown in FIGS. 6, 7, and 8 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the inventory integration system 103, that comprises software or code can be embodied in any non-transitory computer-readable medium for use by or in connection with an instruction execution system such as, for example, a processor 903 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A non-transitory computer-readable medium embodying program code executable in at least one computing device that, when executed by the at least one computing device, causes the at least one computing device to programmatically perform actions that adjust a bandwidth associated with a server computing device that comprises an inventory item to improve an operability of a data center automatically in response to a detection of a condition that impairs the operability of the data center by:
   monitoring an operation of the inventory item employed in an operation of the data center by accessing data generated in association with the inventory item and stored in a data store, wherein the data center comprises the server computing device;
   identifying at least one dependency for the inventory item as monitored, the at least one dependency being a physical item or a virtual constraint necessary for the inventory item to operate;
   generating a health state for the inventory item, wherein the health state comprises a metric generated based at least in part on an operability of the at least one dependency;
   detecting the condition that impairs the operability of the data center based at least in part on the health state generated for the inventory item;
   identifying a plurality of remedial actions that comprise operations capable of being performed programmatically by the at least one computing device in response to detection of the condition; and
   programmatically performing the plurality of remedial actions in association with the inventory item, wherein performance of the plurality of remedial actions automatically improves the operability of the data center and the health state generated for the inventory item, at least a portion of the plurality of remedial actions comprising:
      lowering, by the at least one computing device, the bandwidth of the server computing device of the data center that comprises the inventory item;
      increasing, by the at least one computing device, a bandwidth of another server computing device to assist with a lowered bandwidth of the server computing device;
      reassigning, by the at least one computing device, at least one replacement item to the server computing device for replacement of the inventory item; and
      causing, by the at least one computing device, a replacement of the inventory item with the at least one replacement item.

2. A system for programmatically performing a plurality of remedial actions that, when performed, improve an operability of a data center automatically in response to a detection of a condition that impairs the operability of the data center, the system comprising:
   at least one computing device; and
   at least one memory device comprising program instructions executable in the at least one computing device that, when executed by the at least in computing device, cause the at least one computing device to:
      determine a health state for an inventory item used by a first data center computing device that indicates that the inventory item is causing the condition that is impairing the operability of the data center, wherein the health state comprises a metric generated based at least in part on a dependent health state determined for at least one dependent item, the at least one dependent item being an item that is dependent on the inventory item to properly operate;
      identify a plurality of remedial actions to perform based at least in part on the condition and the inventory item, the remedial actions comprising operations capable of being performed by the at least one computing device to improve the operability of the data center; and
      programmatically perform the plurality of remedial actions, wherein performance of the plurality of remedial actions improve the operability of the data center and the health state of the inventory item, the plurality of remedial actions comprising:
         lowering a bandwidth of the first data center computing device that uses the inventory item;
         increasing a bandwidth of a second data center computing device to assist with a lowered bandwidth of the first data center computing device;
         reassigning at least one replacement item to the first data center computing device for replacement of the inventory item; and
         causing a replacement of the inventory item with the at least one replacement item.

3. The system of claim 2, wherein the inventory item is one of a plurality of inventory items in the data center, wherein the system further comprises program instructions that, when executed by the at least one computing device, cause the at least one computing device to verify an authenticity of a request received from a requesting computing device for a listing of the plurality of inventory items in the data center.

4. The system of claim 2, wherein the health state is determined based at least in part on an estimated lifespan of the inventory item.

5. The system of claim 2, wherein the health state is determined based at least in part on an environment in which the inventory item resides.

6. A computer-implemented method for programmatically performing actions that adjust a bandwidth associated with a server computing device that comprises an inventory item to improve an operability of a data center automatically in response to a detection of a condition that impairs the operability of the data center, comprising:

determining, by at least one computing device comprising at least one hardware processor, that a health metric determined for an inventory item used in the server computing device of the data center is indicative of the condition that affects the operability of the data center, the health metric determined based at least in part on at least one metric determined for at least one other item that is dependent on the inventory item to properly function;

identifying, by the at least one computing device, a plurality of remedial actions to perform in association with the inventory item in response to an identification of the condition affecting the operability of the data center, wherein the plurality of remedial actions are capable of being performed automatically by the at least one computing device to address the condition; and performing, by the at least one computing device, the plurality of remedial actions, at least a portion of the plurality of remedial actions performed comprising:

lowering, by the at least one computing device, a bandwidth of the server computing device of the data center that comprises the inventory item;

increasing, by the at least one computing device, a bandwidth of another server computing device to assist with a lowered bandwidth of the server computing device;

reassigning, by the at least one computing device, at least one replacement item to the server computing device for replacement of the inventory item; and initiating, by the at least one computing device, a transfer of the at least one replacement item to a location associated with the server computing device.

7. The computer-implemented method of claim 6, wherein at least one of the plurality of remedial actions performed comprises communicating, by the at least one computing device, a request to an external resource for the at least one replacement item.

8. The computer-implemented method of claim 7, wherein the request for the at least one replacement item is generated based at least in part on a diversification factor.

9. The computer-implemented method of claim 6, further comprising identifying, by the at least one computing device, the at least one replacement item for the inventory item by querying a data store to identify the at least one replacement item from a plurality of potential replacement items.

10. The computer-implemented method of claim 8, wherein the at least one replacement item is identified based at least in part on an idle state.

11. The computer-implemented method of claim 6, further comprising:

determining, by the at least one computing device, a type of a notification to transmit based at least in part on a level of urgency associated with the condition; and communicating, by the at least one computing device, the notification to an administrator device based at least in part on the type of the notification, wherein the notification comprises the health metric.

12. The computer-implemented method of claim 6, further comprising encoding, by the at least one computing device, the plurality of remedial actions and the health metric in user interface data for rendering a user interface in a display device.

13. The computer-implemented method of claim 6, further comprising:

accessing, by the at least one computing device, a request received from a requesting computing device for a listing of a portion of a plurality of parent inventory items depending on the inventory item to operate;

verifying, by the at least one computing device, an authenticity of the request received from the requesting computing device; and communicating, by the at least one computing device, the listing of the portion of the plurality of parent inventory items to the requesting computing device in response to the authenticity of the request being verified.

14. The non-transitory computer-readable medium of claim 1, wherein the condition detected based at least in part on the health state of the inventory item comprises a bandwidth of the server computing device in the data center falling below a threshold.

15. The non-transitory computer-readable medium of claim 1, wherein the at least one dependency is virtual, the at least one dependency comprising at least one of: an operating system, a virtual server, a software license, or a software application.

16. The system of claim 2, wherein the inventory item is a plurality of inventory items, the plurality of inventory items comprising a plurality of network switches.

17. The system of claim 2, further comprising program instructions that, when executed, cause the at least one computing device to:

identify at least one dependency for the inventory item, the at least one dependency being a physical item or a virtual constraint necessary for the inventory item to operate; and wherein the health state generated for the inventory item is based at least in part on an operability of the at least one dependency.

18. The system of claim 17, wherein the at least one dependency is virtual, the at least one dependency comprising at least one of: an operating system, a virtual server, a software license, or a software application.

19. The system of claim 2, further comprising program instructions that, when executed, cause the at least one computing device to:

identify at least one parent inventory item that includes the inventory item; and generate or adjust a health metric of the at least one parent inventory item using the health metric generated for the inventory item.

20. The system of claim 2, further comprising program instructions that, when executed, cause the at least one computing device to:

determine a temperature of an environment in which the inventory item resides; and adjust the metric for the inventory item based at least in part on the temperature.

\* \* \* \* \*